(12) United States Patent
Whitely (10) Patent No.: US 10,172,738 B2
(45) Date of Patent: Jan. 8, 2019

(54) THERMOTHERAPEUTIC PAD FOR PROVIDING HEAT OR COLD TO A BODY PART

(75) Inventor: Jeffrey Thomas Whitely, Millgrove (CA)

(73) Assignees: RAPID AID LTD., Mississauga, Ontario (CA); RAPID AID CORP., Mississauga, Ontario (CA)

( * ) Notice: Subject to any disclaimer, the term of this patent is extended or adjusted under 35 U.S.C. 154(b) by 656 days.

(21) Appl. No.: 12/668,610

(22) PCT Filed: May 27, 2008

(86) PCT No.: PCT/CA2008/001021
§ 371 (c)(1),
(2), (4) Date: Jan. 11, 2010

(87) PCT Pub. No.: WO2009/009862
PCT Pub. Date: Jan. 22, 2009

(65) Prior Publication Data
US 2010/0217363 A1 Aug. 26, 2010
US 2012/0004712 A2 Jan. 5, 2012

(30) Foreign Application Priority Data
Jul. 13, 2007 (CA) .................... 2593685

(51) Int. Cl.
*A61F 7/02* (2006.01)
(52) U.S. Cl.
CPC .......... *A61F 7/02* (2013.01); *A61F 2007/023* (2013.01); *A61F 2007/0207* (2013.01); *A61F 2007/0231* (2013.01)

(58) Field of Classification Search
CPC ........ A61F 2007/0207; A61F 2007/023; A61F 2007/0231; A61F 7/02
(Continued)

(56) References Cited

U.S. PATENT DOCUMENTS 1,385,074 A 7/1921 Ferguson
1,920,853 A 8/1933 Ferguson
(Continued)

FOREIGN PATENT DOCUMENTS

WO WO 00/07529 2/2000

OTHER PUBLICATIONS

International Search Report dated Sep. 15, 2008 in corresponding international application No. PCT/CA2008/001020.
(Continued)

*Primary Examiner* — Joseph Stoklosa
*Assistant Examiner* — Samantha Good
(74) *Attorney, Agent, or Firm* — F. Chau & Associates, LLC.

(57) ABSTRACT

A thermotherapeutic pad for applying heat or cold to a body part. The pad has a material for releasing or absorbing heat and a thermally conductive envelope for containing the granular material. The pad also has a holder for removably holding a cold pack adjacent to the envelope. The thermotherapeutic pad may provide heat by heating the material and placing the envelope against the body part, and the thermotherapeutic pad may absorb heat by placing a cooled cold pack into the holder and placing the portion of the pad comprising the cold pack against the body part.

10 Claims, 6 Drawing Sheets (58) Field of Classification Search
USPC ......... 607/112, 108, 96, 111; 62/530; 602/2;
165/46; 126/204–210
See application file for complete search history.

(56) References Cited

U.S. PATENT DOCUMENTS

| | | | |
|---|---|---|---|
| 3,840,918 A * | 10/1974 | Shave | 5/640 |
| 3,951,127 A | 4/1976 | Watson et al. | |
| 4,057,047 A | 11/1977 | Gossett | |
| 4,451,383 A | 5/1984 | Arrhenius | |
| 4,834,802 A | 5/1989 | Prier | |
| 4,856,651 A | 8/1989 | Francis, Jr. | |
| 4,858,259 A | 8/1989 | Simmons et al. | |
| 5,020,711 A | 6/1991 | Kelley | |
| 5,050,596 A * | 9/1991 | Walasek et al. | 607/111 |
| 5,148,804 A | 9/1992 | Hill et al. | |
| 5,300,104 A * | 4/1994 | Gaudreault et al. | 607/114 |
| 5,305,733 A | 4/1994 | Walters | |
| 5,534,020 A | 7/1996 | Cheney, III et al. | |
| 5,571,155 A | 11/1996 | Bastille | |
| 5,603,727 A * | 2/1997 | Clark et al. | 607/108 |
| 5,697,962 A | 12/1997 | Brink et al. | |
| 6,020,040 A | 2/2000 | Cramer et al. | |
| 6,083,254 A * | 7/2000 | Evans | 607/114 |
| 6,083,256 A * | 7/2000 | Der Ovanesian | 607/114 |
| 6,103,139 A | 8/2000 | Kohout | |
| 6,318,359 B1 | 11/2001 | Schmidt et al. | |
| 6,714,821 B1 * | 3/2004 | Duda et al. | 607/98 |
| 7,182,777 B2 * | 2/2007 | Mills | 607/108 |
| 2004/0243203 A1 | 12/2004 | Lavine | |
| 2005/0028806 A1 * | 2/2005 | Kumamoto et al. | 126/263.02 |
| 2005/0256555 A1 * | 11/2005 | Fisher et al. | 607/96 |

OTHER PUBLICATIONS

Notification of Transmittal of International Preliminary Report on on Patentability dated Oct. 20, 2009 in corresponding international application No. PCT/CA2008/001020.

Canadian Office Action dated Jan. 5, 2009 in Canadian Patent No. 2,305,093 which corresponds to U.S. Pat. No. 6,318,359.

* cited by examiner

THERMOTHERAPEUTIC PAD FOR PROVIDING HEAT OR COLD TO A BODY PART

This application is a 371 of a PCT International Application No. PCT/CA08/01021, filed on May 27, 2008.

FIELD OF THE INVENTION

This invention relates to thermotherapeutic pads. In particular, the invention relates to thermotherapeutic pads that may be applied to parts of the body to provide alternatively a hot or cold sensation and/or therapeutic effect.

BACKGROUND OF THE INVENTION

It is known that heat transfer articles and devices can be used to provide temporary relief from aches, pains, and muscle soreness in limbs. In common use, an article or device is heated in some manner and placed on the skin. An article that relies on an external energy source for heat may for example be heated in a conventional oven or, more typically nowadays, in a microwave oven.

An example of such an article is a bag or envelope containing grains of cereal such as oats, as is well known. A thermally conductive envelope, for example made of cotton, may be filled with oats for heating in a conventional oven or microwave oven. In use, the heat generated in the oats by the energy source is transferred to the user's skin and subcutaneous tissue, for soothing and/or therapeutic relief.

Therapeutic articles which provide a cooling effect are also well known to provide a soothing effect for swelling or pain when applied to the skin. Such an article may be cooled in a freezer and then placed in contact with the skin, absorbing heat from the skin to provide the desired cooling effect. The envelope containing oats as described above is an example of such a therapeutic cooling article. However, using a cotton envelope containing oats as a therapeutic cooling article, often results in a damp sensation when the article is placed against the skin. A therapeutic cooling article may alternatively consist of a gel pack filled with a gel having a high thermal inertia and a low freezing point, and is available in both reusable and one-time use forms. When cooled the gel pack assumes the temperature of the freezer, which can be colder than human skin can comfortably accommodate, and as such a gel pack often must be wrapped in a towel or other fabric to partially insulate the cold of the gel pack from the hand or body in order to prevent discomfort.

SUMMARY OF THE INVENTION

The present invention provides a thermotherapeutic pad for providing heat or cold to a body part comprising a thermally conductive envelope containing a material (e.g. substantially free flowing grains of cereal) for releasing heat or absorbing heat, or both, a holder for removably holding a cold pack adjacent to the envelope, the holder being disposed on a first face of the thermotherapeutic pad, and optionally a cold pack (e.g. gel pack), whereby the thermotherapeutic pad may provide heat by heating the material and placing the envelope against the body part, and the thermotherapeutic pad may absorb heat by cooling a cold pack and placing the cooled cold pack into the holder and placing at least a portion of the holder or the cold pack, or both, against the body part.

The holder may comprise a pocket formed by a layer of thermally conductive fabric or a hook and loop fastener for releasably closing the holder. The holder may also expose at least a portion of the cold pack.

The thermotherapeutic pad may further comprise a sleeve for removably receiving a user's hand on a second face of the thermotherapeutic pad opposite the first face, whereby the sleeve may be used to maintain the user's hand in position while holding the pad against the body part.

BRIEF DESCRIPTION OF THE DRAWINGS

In drawings which illustrate by way of example only a preferred embodiment of the invention.

DETAILED DESCRIPTION OF THE INVENTION

Figure 1:
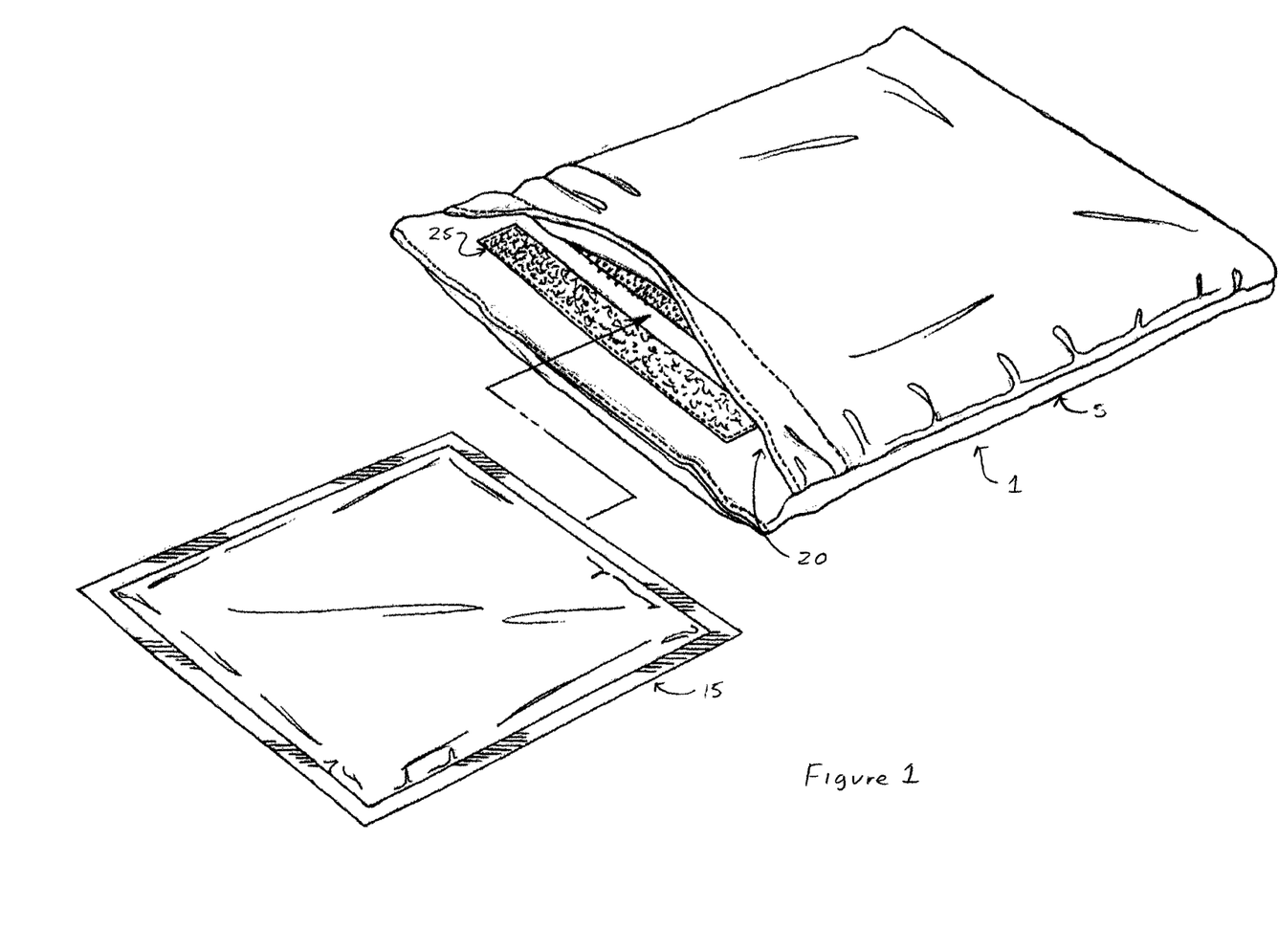
FIG. 1 is a perspective view of a thermotherapeutic pad with a removable cold pack according to the invention.
Figure 2:
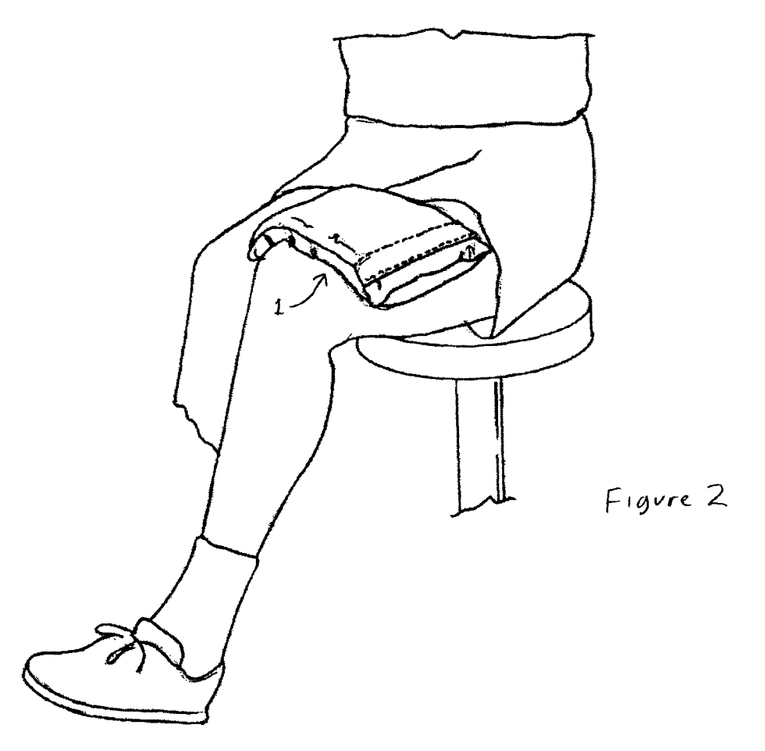
FIG. 2 is a perspective view of a thermotherapeutic pad according to the invention positioned on a user's leg.
Figure 3:
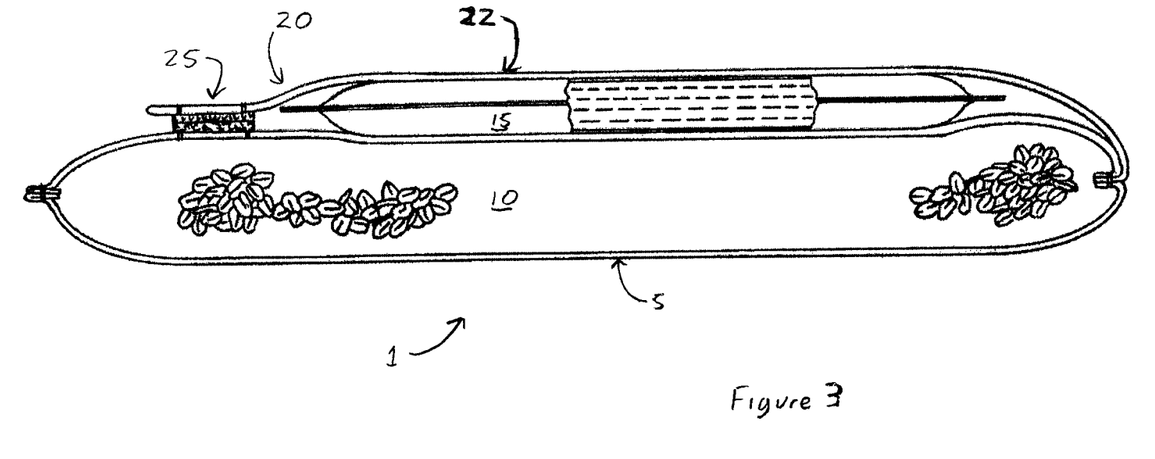
FIG. 3 is a side cross-sectional view of the thermotherapeutic pad of FIG. 1.

In one embodiment, illustrated in FIGS. 1 to 3, the thermotherapeutic pad 1 consists of a thermally conductive envelope 5 enclosing a quantity of free flowing grains of cereal 10 and a pouch or pocket 20 adapted to contain a removable cold pack 15.

The envelope 5 is preferably made of a soft flexible material, for example a cotton or flannel fabric. The envelope 5 should be resistant to both hot and cold temperatures and being heated in a microwave oven. The envelope 5 may be sealed, for example sewn about its peripheral edges as shown, with a suitable quantity of cereal grains 10 inside. The envelope 5 may be formed in any of a variety of shapes. The embodiment shown is generally rectangular, but other shapes may be used, including a tube-like shape.

The quantity of grains of cereal 10 enclosed in the thermotherapeutic pad 1 is typically selected to have a high thermal inertia. Preferably, the grains are rounded and free flowing, to more readily conform to the body part on which the thermotherapeutic pad 1 is placed. In the preferred embodiment, the grains of cereal 10 can flow freely within the envelope 5 as the envelope 5 is deformed or bent. In one embodiment the grains of cereal are oats, which may have a water content within the range of 9 to 14% by weight of the oat total weight, but other granular materials may be used.

The quantity of grains of cereal 10 enclosed within the envelope 5 is selected so the envelope 5 is substantially filled but is able to conform to the body part on which the pad 1 is being applied. In addition, the envelope 5 preferably contains a sufficient quantity of grains of cereal 10 to avoid parts of the envelope 5 being devoid of oats.

The thermotherapeutic pad 1 described thus far is conventional. A person skilled in the art will appreciate that other materials may be used in place of the grains of cereal 10 to provide thermal inertia. Examples of other materials that may be used are sand, plastic beads, flax seeds, cherry pits and corn.

According to the invention, the thermotherapeutic pad 1 provides a holder for holding a removable cold pack 15 against the envelope. The holder may for example comprise a pouch or pocket 20 formed by a fabric layer 22 for containing the removable cold pack 15, which may be placed in the pocket 20 provided on the exterior of the envelope 5. The pocket 20 is preferably closeable with a fastening means 25, such as a Velcro (Trademark) hook and loop fastener strip or by any other suitable releasable fastener including without limitation grommets or buttons. The cold pack 15 can be any disposable or reusable pack that exhibits sufficient thermal inertia when cooled to absorb heat from a body part. Preferably, the cold pack 15 is flexible to conform to the body part to which it is applied when cooled. The fabric layer 22 is formed from a fabric which is thermally conductive, for example the same fabric as the envelope 5, so that when a cooled cold pack 15 is disposed in the pocket 20 heat can be transferred from a body part through the fabric layer 22 to the cold pack 15.

Figure 6:
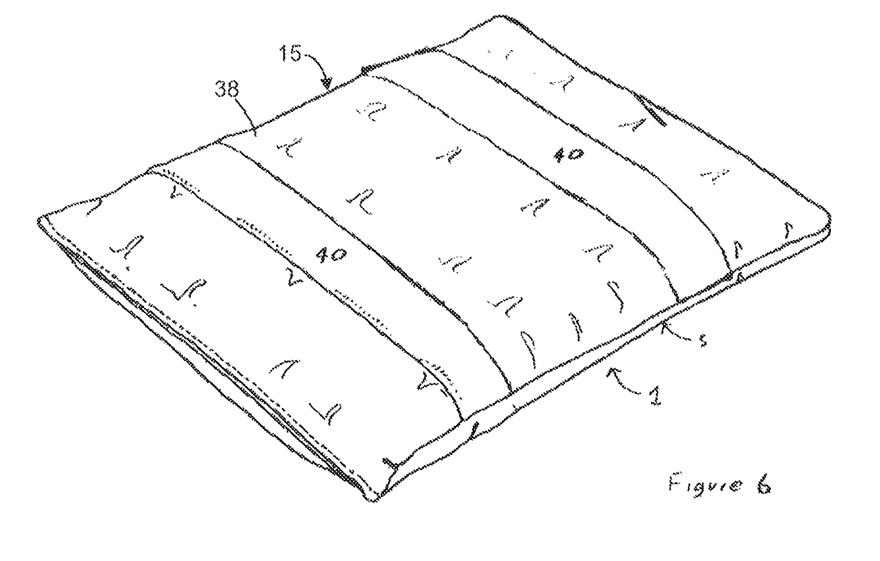
FIG. 6 is a perspective view of a further embodiment of a thermotherapeutic pad according to the invention having straps to hold the cold pack.

The holder may alternatively comprise a sleeve, one or more ties, straps, hook and loop fastener strips or otherwise as suitable to hold the removable cold pack 15 adjacent to the envelope 5. In these embodiments the cooled cold pack 15 may have exposed portions 38 that can be placed in direct contact with the body part, in which case the holder is not necessarily formed from a thermally conductive material. In one embodiment, illustrated in FIG. 6, straps 40 are used to hold the removable cold pack to the envelope 5.

In the preferred embodiment, the holder comprises a pocket 20 formed from a fabric layer 22 sown into the seams along three of the edges of the envelope 5.

In the preferred embodiment, the cold pack 15 is a gel pack. The gel pack may be made from a sealed cold-resistant plastic envelope containing a high thermal inertia gel such as a cool flexible gel, as is well known.

In use, the thermotherapeutic pad 1 can be used to provide alternatively a cold or hot sensation and/or therapeutic effect to a body part to which it is applied. A single pad can be reused repeatedly to either provide heat to the body part or absorb heat from the body part.

To provide a heating sensation, the cold pack 15 is removed from (or left out of) the pocket 20 of the thermotherapeutic pad 1. The pad 1 is heated using any suitable means, for example by placing it in a microwave oven for a prescribed interval. The heated thermotherapeutic pad 1 can then be placed against the body part to provide a heating sensation and impart heat to the skin and underlying tissue. The heating sensation of a heated thermotherapeutic pad 1 using oats as the grain of cereal is sometimes known as a "moist heat".

The cold pack 15 may be stored in a freezer until the thermotherapeutic pad 1 is needed, to provide a cooling sensation.

To provide a cooling sensation or absorb heat from a body part, the cold pack 15 may be removed from freezer and placed back in the pocket 20 of the thermotherapeutic pad 1, and the fabric layer 22 is placed against the body part. The envelope 5 containing cereal grains 10 thus provides a flexible backing that helps to hold the cold pack 15 against the body part and maintain the shape of the cold pack 15 conforming to the body part on which it is placed, while insulating the user's hand from the cold gel inside the cold pack, making use of the thermotherapeutic pad 1 more comfortable.

After use, the cold pack 15 may be returned to the freezer for re-cooling and storage. Alternatively, the cold pack 15 may be stored with the thermotherapeutic and placed in the freezer immediately prior to use.

The cold pack 15 may alternatively be left in the pocket 20 of the thermotherapeutic pad 1 and the combination of the cold pack 15 and envelope 5 cooled in the freezer. In this case, for rapid or more severe cooling the face of the thermotherapeutic pad 1 providing the pocket 20 (with inserted cold pack 15) is placed against the skin, and for less abrupt cooling (for example if the cooling starts to cause pain or discomfort) the pad 1 may be reversed so that the envelope 5 is against the skin. The cereal grains 10 typically have less thermal inertia than the gel, and thus provide a more tempered cooling effect.

A person skilled in the art will appreciate that methods of cooling other than a freezer may be used, such as a refrigerator. Alternatively, single use cold packs such as chemical packs which do not require a freezer may be used to provide the cooling effect.

The combination of the cold pack 15 and the grains of cereal 10 in the envelope can be used to provide both a moist heat using heated grains of cereal 10 and a cooling sensation using the cold pack 15 in the pocket 20.

Figure 4:
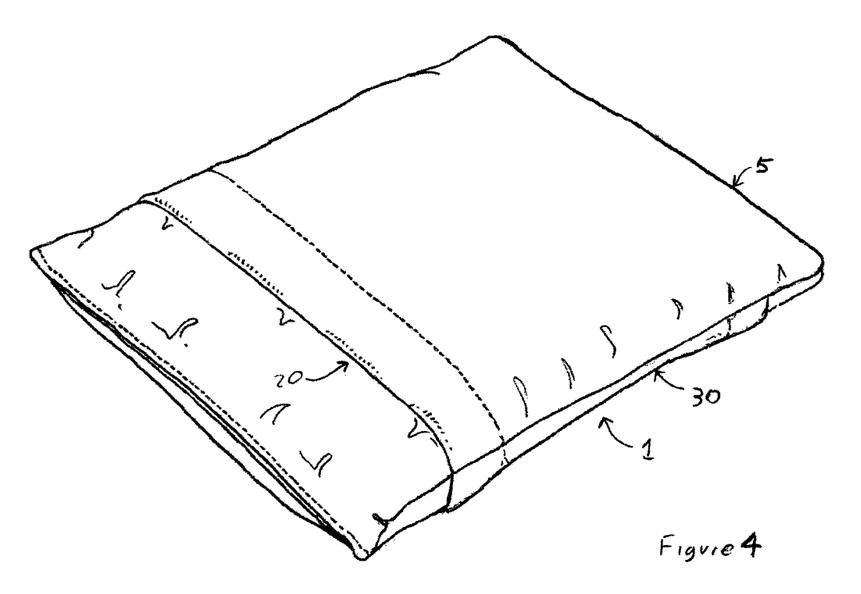
FIG. 4 is a perspective view of a further embodiment of a thermotherapeutic pad according to the invention having a sleeve to facilitate holding the pad.
Figure 5:
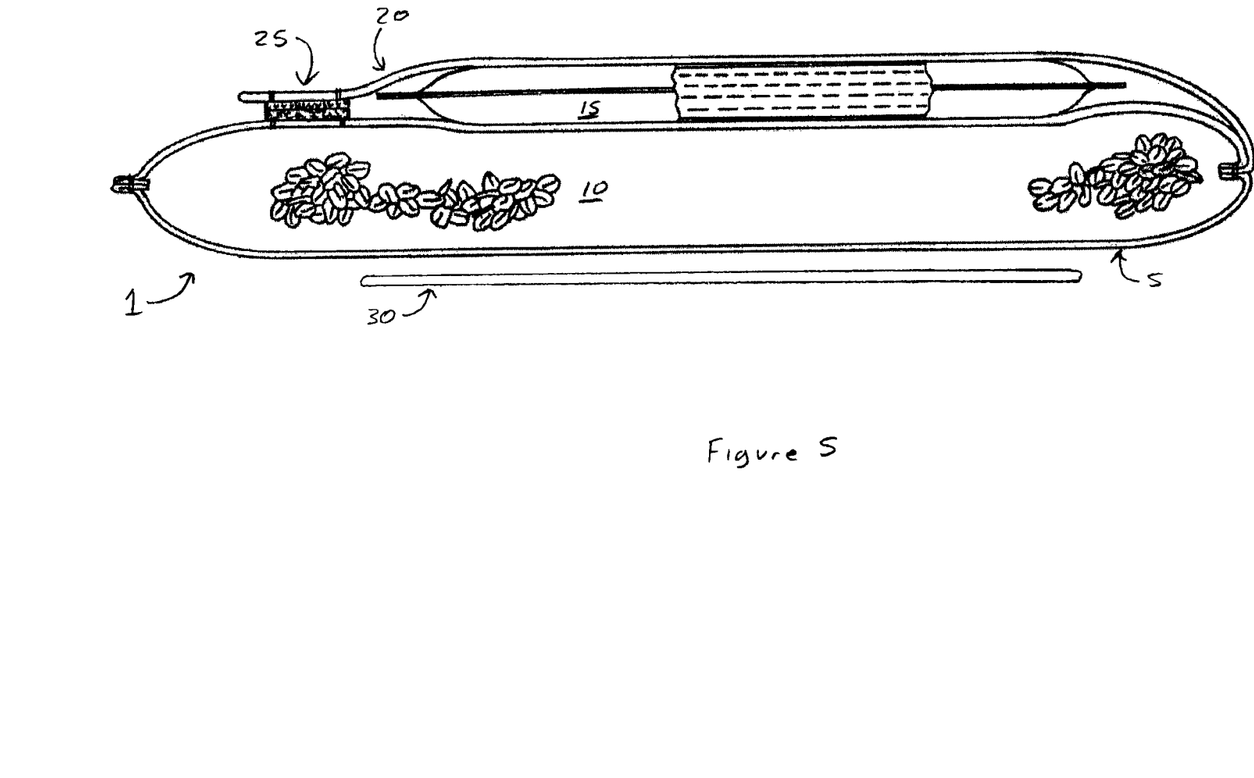
FIG. 5 is a side cross-sectional view of the embodiment of the thermotherapeutic pad of FIG. 4.

In a further embodiment illustrated in FIGS. 4 and 5, the thermotherapeutic pad 1 may provide a sleeve 30 on the face opposite the face of the envelope 5 bearing the pocket 20. The sleeve 30 may be open at both ends as shown, or may have one closed end. In this embodiment the user of the pad may place their hand in the sleeve 30 to support the pad 1 during use, which helps to position and maintain the pad 1 against the body and avoids the muscle fatigue associated with a user having to grip the envelope 5 in order to hold it in position on the body part. The sleeve 30 may alternatively be a pouch, a strap or other means for supporting the thermotherapeutic pad 1 on a user's hand.

Various embodiments of the present invention having been thus described in detail by way of example, it will be apparent to those skilled in the art that variations and modifications may be made without departing from the invention.

What is claimed is:

1. A thermotherapeutic pad for providing heat or cold to a body part comprising:
   a thermally conductive envelope containing a material for releasing heat, the material comprising substantially free flowing grains of cereal, and
   a pocket formed by a layer of thermally conductive material for removably holding a cold pack adjacent to the envelope, the pocket being disposed on a first face of the envelope, whereby the thermotherapeutic pad may provide heat by heating the material and placing the envelope against the body part, and the thermotherapeutic pad may absorb heat by cooling the cold pack and placing the cooled cold pack into the pocket and placing at least a portion of the pocket in direct contact with the body part.

2. The thermotherapeutic pad of claim 1 further comprising the cold pack.

3. The thermotherapeutic pad of claim 2 wherein the pocket for removably holding the cold pack comprises a hook and loop fastener for releasably closing the pocket.

4. The thermotherapeutic pad of claim 2 further comprising a sleeve for removably receiving a user's hand on a second face of the envelope opposite the first face, whereby the sleeve may be used to maintain the user's hand in position while holding the pad against the body part.

5. The thermotherapeutic pad of claim 2 wherein the cold pack for absorbing heat comprises a gel pack.

6. The thermotherapeutic pad of claim 1 wherein the pocket for removably holding the cold pack comprises a hook and loop fastener for releasably closing the pocket.

7. The thermotherapeutic pad of claim 1 further comprising a sleeve for removably receiving a user's hand on a second face of the envelope opposite the first face, whereby the sleeve may be used to maintain the user's hand in position while holding the pad against the body part.

8. The thermotherapeutic pad of claim/wherein the material has a water content in the range of 9 to 14% by weight.

9. A thermotherapeutic pad for providing heat or cold to a body part comprising:
   a thermally conductive envelope containing a material for releasing heat, the material comprising substantially free flowing grains of cereal having a water content in the range of 9 to 14% by weight,
   a cold pack,
   a pocket removably holding the cold pack adjacent to the envelope, the pocket being disposed on a first face of the envelope and being formed by a layer of thermally conductive fabric, and
   a sleeve for removably receiving a user's hand on a second face of the envelope opposite the first face,
   whereby the thermotherapeutic pad may provide heat by heating the material and placing the envelope against the body part, and the thermotherapeutic pad may absorb heat by cooling the cold pack and placing the cooled cold pack into the pocket and placing at least a portion of the pocket in direct contact with the body part, and whereby the sleeve may be used to maintain the user's hand in position while holding the pad against the body part.

10. The thermotherapeutic pad of claim 9 wherein the cold pack for absorbing heat comprises a gel pack.

\* \* \* \* \*